United States Patent
Hemy et al.

(10) Patent No.: US 10,773,034 B2
(45) Date of Patent: *Sep. 15, 2020

(54) DRY POWDER INHALER

(71) Applicant: Presspart Manufacturing Ltd., Lancashire (GB)

(72) Inventors: Julian Hemy, Cheshire (GB); Richard Turner, Lancashire (GB); Hans-Peter Schmelzer, Meerbusch (DE); Hans-Jürgen Neugebauer, Warburg (DE); Dietmar Schmitz, Brilon (DE); Stefan Hoffmann, Tönisvorst (DE); Ameet Sule, Maharashtra (IN); Sunita Sule, Maharashtra (IN); Matthias Seiler, Düsseldorf (DE); George Alexander Bostock, Cambridge (GB); Aki Hannu Einari Laakso, Cambridge (GB); Michael Worth, Cambridge (GB)

(73) Assignee: Presspart Manufacturing Ltd., Lancashire (GB)

( * ) Notice: Subject to any disclaimer, the term of this patent is extended or adjusted under 35 U.S.C. 154(b) by 243 days.

This patent is subject to a terminal disclaimer.

(21) Appl. No.: 15/761,253

(22) PCT Filed: Oct. 21, 2016

(86) PCT No.: PCT/EP2016/075477
§ 371 (c)(1),
(2) Date: Mar. 19, 2018

(87) PCT Pub. No.: WO2017/068171
PCT Pub. Date: Apr. 27, 2017

(65) Prior Publication Data
US 2018/0264208 A1 Sep. 20, 2018

(30) Foreign Application Priority Data
Oct. 23, 2015 (EP) .................................... 15191215

(51) Int. Cl.
A61M 15/00 (2006.01)
A61M 11/00 (2006.01)
A61K 9/00 (2006.01)

(52) U.S. Cl.
CPC ...... A61M 15/0005 (2014.02); A61M 11/002 (2014.02); A61M 15/003 (2014.02);
(Continued)

(58) Field of Classification Search
CPC .............. A61M 15/00; A61M 15/0001; A61M 15/0005; A61M 15/0021; A61M 15/0028;
(Continued)

(56) References Cited

U.S. PATENT DOCUMENTS 4,069,819 A    1/1978   Valentini et al.
5,752,505 A *  5/1998   Ohki ................ A61M 15/0028
                                                  128/203.15
(Continued)

FOREIGN PATENT DOCUMENTS

DE    102014005646 A1    7/2015
DE    102014005647 A1    7/2015
(Continued)

OTHER PUBLICATIONS

International Search Report and Written Opinion dated Dec. 6, 2016 in corresponding PCT application No. PCT/EP2016/075477.
Behara et al., "Development of a High Efficiency Dry Powder Inhaler: Effects of Capsule Chamber Design and Inhaler Surface Modifications", Pharmaceutical Research, vol. 31, pp. 360-372, 2014.

*Primary Examiner* — Joseph D. Boecker
(74) *Attorney, Agent, or Firm* — Nields, Lemack & Frame, LLC

(57) ABSTRACT

The present invention relates to an inhaler device for delivering a dose of medicament in dry powder form from a container to a patient in need thereof. The inhaler comprises first and second airflow paths (80, 85) which are arranged such that during inhalation, a capsule (40) having a longi- (Continued)

tudinal axis and first and second end sections (90, 95) delimiting the capsule on opposing ends located in a capsule chamber (30) performs an oscillating movement in the capsule chamber parallel to its longitudinal axis between first and second sidewall portions (60, 65) of the capsule chamber.

17 Claims, 9 Drawing Sheets

(52) U.S. Cl.
CPC .... *A61M 15/0021* (2014.02); *A61M 15/0035* (2014.02); *A61K 9/0075* (2013.01); *A61M 15/0041* (2014.02); *A61M 2202/0007* (2013.01); *A61M 2202/064* (2013.01); *A61M 2206/16* (2013.01)

(58) Field of Classification Search
CPC ............ A61M 15/003; A61M 15/0035; A61M 15/0041; A61M 15/0091; A61M 2202/064; A61M 2206/16
See application file for complete search history.

(56) References Cited

U.S. PATENT DOCUMENTS

| | | | |
|---|---|---|---|
| 10,456,535 B2* | 10/2019 | Hemy | ............... A61M 15/0005 |
| 2007/0240714 A1 | 10/2007 | Dunne et al. | |
| 2012/0247465 A1 | 10/2012 | Wachtel et al. | |
| 2013/0074841 A1 | 3/2013 | Schuckmann | |
| 2015/0107589 A1* | 4/2015 | Longest | ............ A61M 15/0045 |
| | | | 128/203.15 |

FOREIGN PATENT DOCUMENTS

| | | |
|---|---|---|
| EP | 1488819 A1 | 12/2004 |
| EP | 1603615 B1 | 12/2005 |
| EP | 2739334 A1 | 6/2014 |
| GB | 2460281 A | 11/2009 |
| WO | 2013/016787 A1 | 2/2013 |
| WO | 2013/169473 A1 | 11/2013 |
| WO | 2015/127258 A2 | 8/2015 |

* cited by examiner

DRY POWDER INHALER

The present invention relates to an inhaler device for delivering a dose of medicament in dry powder form from a container to a patient in need thereof.

BACKGROUND OF THE INVENTION

Inhalers are commonly used to deliver drugs into the lung of a patient in need thereof. Different types of inhalers have been developed and are available on the market, amongst which dry powder inhalers (DPIs) are becoming attractive in the treatment of various respiratory problems such as asthma, bronchitis or chronic obstructive pulmonary disease (COPD) and for the delivery of non-asthma drugs delivered via inhalation.

In dry powder inhalers, the dose of medicament is present in dry powder form and usually pre-packed in containers such as a capsule. Blister-based dry powder inhalers are also known.

In capsule-based dry powder inhalers, a capsule is placed into a capsule chamber of the inhaler before inhalation and opened, e.g. by piercing the capsule at its ends. Subsequently, the patient inhales through a nosepiece or mouthpiece whereupon an inhalation airflow is generated within the inhaler. The medicament in dry powder form is released from the capsule, entrained into the inhalation airflow and inhaled by the patient.

For dose consistency, it is desirable that as much as possible of the dose of medicament is released from the capsule, inhaled by the patient and delivered to the site of action in the lung.

Medicaments in dry powder form contained in capsules usually consist of a blend of the active ingredient and a bulking agent, e.g. lactose. The powder blend is usually present in form of big agglomerates which are usually a mixture of big and small particles. However, big particles often show a poor release from the capsule and/or a poor lung uptake. Thus, in conventional dry powder inhalers it is desired to break and/or de-agglomerate larger particles into smaller, breathable particles prior or during inhalation in order to allow for an efficient release from the capsule as well as an efficient lung uptake. Particles with a size of not more than 5 µm are believed to be particularly advantageous for an efficient lung uptake.

One approach of breaking down/de-aggregate larger particles inside the capsule during inhalation is to set the capsule into motion thereupon causing impacts between the capsule and the capsule chamber, whereby stronger impacts are believed to lead to a better breakdown of the powder particles and consequently to a more efficient release from the capsule.

Different techniques and capsule chamber geometries have been developed and applied in order to set the capsule into motion during inhalation.

EP 2 739 334 A1 relates to a capsule-based dry powder inhaler wherein the capsule is subjected to a horizontal, propeller-like movement. The inhaler is equipped with means that allow the capsule to serve as an air flow control valve and at the same time, this effect causes repetitive impacts of the capsule against the walls of the chamber in order to improve the outflow of the powder and its breakdown.

EP 1 603 615 B1 relates to an inhaler comprising a capsule chamber having a form and a volume greater than the capsule such that the capsule rotates during inhalation in a propeller-like motion.

U.S. Pat. No. 4,069,819 A relates to a capsule based dry powder inhaler comprising a nebulization chamber for a capsule in which an air passageway is formed in such manner as to set the flowing air in vortical motion such as to cause the capsule, under the action of the flowing air, to make movements of rotation, precession and vibration about and along its longitudinal axis.

However, these approaches often lead to randomly occurring, hardly reproducible and relatively weak impacts between the capsule and the capsule chamber which may cause an unsatisfactory and irreproducible breakdown of the powder and thereby a poor emptying of the capsule.

It is an object of the present invention to provide an inhaler device that overcomes the above problems. In particular, it is an object of the present invention to provide an inhaler device that shows an improved emptying of the capsule during inhalation. It is further an object of the present invention to provide a method for delivering a dose of medicament in dry powder form from a capsule to a patient.

SUMMARY OF THE INVENTION

The above mentioned objects are achieved by an inhaler device comprising an inhaler housing comprising at least one air inlet duct. The inhaler device further comprises an elongated capsule chamber adapted for receiving a capsule which contains a dose of medicament in dry powder form. The capsule chamber has a longitudinal axis and is defined by a wall arrangement including a first and a second supporting wall portion opposing each other in a direction perpendicular to the longitudinal axis of the capsule chamber. The wall arrangement further includes first and second sidewall portions opposing each other in the direction of the longitudinal axis of the capsule chamber. The inhaler device further comprises a mouthpiece portion through which the medicament in dry powder form is dispensable and at least first and second airflow paths which extend between the at least one air inlet duct, the capsule chamber and the mouthpiece portion to enable an inhalation airflow formed upon inhalation to flow through the at least one air inlet duct via the capsule chamber and the mouthpiece portion such that the dose of medicament is entrained in air and dispensed through the mouthpiece portion. The first and second airflow paths are arranged such that during inhalation, a capsule having a longitudinal axis and first and second end sections delimiting the capsule on opposing ends located in the capsule chamber performs an oscillating movement in the capsule chamber parallel to the longitudinal axis of the capsule chamber between the first and the second sidewall portions when an airflow is initiated through the first and the second airflow paths in a direction from the at least one air inlet duct towards the mouthpiece portion.

The first airflow path comprises at least a first intermediate duct extending from the at least one air inlet duct to a first capsule chamber inlet adjacent to the first sidewall portion, and at least a first outlet duct extending from a first capsule chamber outlet adjacent to the first sidewall portion to the mouthpiece portion. The second airflow path preferably comprises at least a second intermediate duct extending from the at least one air inlet duct to a second capsule chamber inlet adjacent to the second side wall, and at least a second outlet duct extending from a second capsule chamber outlet adjacent to the second sidewall portion to the mouthpiece portion. The first capsule chamber inlet is formed between the first supporting wall portion and the first sidewall portion. The second capsule chamber inlet is formed between the first supporting wall portion and the second sidewall portion. The first capsule chamber outlet is formed between the second supporting wall portion and the first sidewall portion. The second capsule chamber outlet is formed between the second supporting wall portion and the second sidewall portion.

Preferably, the first supporting wall portion has an extension in a direction extending parallel to the longitudinal axis of the capsule chamber with a length "A" and the second supporting wall portion has an extension in a direction extending parallel to the longitudinal axis of the capsule chamber with a length "B".

Preferably, while performing the oscillating movement, impacts between the capsule, in particular between its first and second end sections, and the first and second sidewall portions of the capsule chamber are generated such that a dose of medicament in dry powder form contained within the capsule is broken down into fine, breathable particles and finely dispersed inside the capsule, whereupon the fine particles are released into the airstream.

Preferably, the capsule containing a dose of medicament in dry powder form comprises a central section between said first and second end sections. Preferably, the central section is in cylindrical form. The central section of the capsule is preferably adapted to be supported by the first and second supporting wall portions against a movement in a plane extending perpendicular to the longitudinal axis. According to this embodiment, after being inserted into the capsule chamber, the capsule moves only parallel to its longitudinal axis between the first and second sidewall portions.

According to a preferred embodiment, the inhaler device further comprises a moveable piercing means for piercing a capsule located in the capsule chamber. The piercing means is preferably located in the first and second sidewall portions of the capsule chamber. According to this embodiment, the capsule is preferably pierced at its first and second end sections. Alternatively, the capsule may be opened by cutting means.

It is preferred that the distance between the first supporting wall portion and the first sidewall portion (in the following termed "size of the first capsule chamber inlet") is identical to the distance between the first supporting wall portion and the second sidewall portion (in the following termed "size of the second capsule chamber inlet"). Or in other words: The first capsule chamber inlet and the second capsule chamber inlet are of the same size. It is further preferred that the distance between the second supporting wall portion and the first sidewall portion (in the following termed "size of the first capsule chamber outlet") is identical to the distance between the second supporting wall portion and the second sidewall portion (in the following termed "size of the second capsule chamber outlet"). Or in other words: The first capsule chamber outlet and the second capsule chamber outlet are of the same size. It is further preferred that the capsule inserted into the capsule chamber has an extension between its first and second end sections that is larger than the larger one of said sizes of the first and second capsule chamber inlets and first and second capsule chamber outlets. In this way, the capsule acts as an airflow barrier preventing air to flow from the first airflow path to the second airflow path (or vice versa) within the capsule chamber.

Is it particularly preferred that the capsule inserted into the capsule chamber has an extension between its first and second end sections that is larger than the larger one of the sum of the length "A" and the size of the first or second capsule chamber inlet and the sum of the length "B" and the size of the first or second capsule chamber outlet. This means that if, for example, the sum of the length "A" and the size of the first or second capsule chamber inlet is larger than the sum of the length "B" and the size of the first or second capsule chamber outlet, the capsule has an extension between its first and second end sections that is larger than the sum of the length "A" and the size of the first or second capsule chamber inlet.

In this way, a constriction zone is created within the capsule chamber between the first or second sidewall portion of the capsule chamber and the first or second end section of the capsule. Thus, according to the principle of continuity, air flowing through the capsule chamber has an increased velocity when flowing through said constriction zone. According to the principle of conservation of mechanical energy, said gain in kinetic energy—due to the increased velocity of the air flowing through the constriction zone—leads to a drop in pressure in the capsule chamber at the proximity of the first or second sidewall. This effect is also known as the Venturi effect. Consequently, due to the reduced pressure in the capsule chamber at the proximity of the first or second sidewall portion, the capsule is moved towards the first or second sidewall portion during inhalation.

According to another embodiment, the first capsule chamber inlet and the second capsule chamber inlet are of different size and/or the first capsule chamber outlet and the second capsule chamber outlet are of different size. Also in this case it is preferred that the capsule inserted into the capsule chamber has an extension between its first and second end sections that is larger than the largest one of said sizes of the first and second capsule chamber inlets and first and second capsule chamber outlets. In this way, the capsule acts as an airflow barrier preventing air to flow from the first airflow path to the second airflow path (or vice versa) within the capsule chamber.

According to this embodiment, it is particularly preferred that the capsule inserted into the capsule chamber has an extension between its first and second end sections that is larger than the largest one of the sum of the length "A" and the size of the first or second capsule chamber inlet and the sum of the length "B" and the size of the first or second capsule chamber outlet. In this way, a constriction zone is created within the capsule chamber between the first or second sidewall and the first or second end section of the capsule.

According to a preferred embodiment of the inhaler device according to the present invention, the first and second intermediate ducts taper in direction from the at least one air inlet duct to the first and second capsule chamber inlets. Thereby, according to the principle of continuity, air flowing from the at least one air inlet duct to the capsule chamber is accelerated when flowing through first and second (tapering) intermediate ducts.

According to a further preferred embodiment of the inhaler according to the present invention, first and second outlet ducts are not curved. Alternatively, according to another preferred embodiment of the inhaler according to the present invention, first and/or second outlet ducts are curved (bent). It is preferred that both of the first and second outlet ducts are curved (bent). Preferably, first and second outlet ducts are connected to form one continuous curve, where the mouthpiece portion is connected to the apex of the curve formed by the first and second outlet ducts. In an embodiment where the inhaler comprises a classifier chamber (see below), the classifier chamber is connected to the apex of the curve formed by the first and second outlet ducts and the mouthpiece portion is connected to the apex of the curve formed by the first and second classifier ducts. According to another preferred embodiment of the inhaler according to the present invention, first and/or second outlet ducts are curved and connected to form a wavy form comprising two crests and one trough. Preferably, the mouthpiece portion is connected to the trough. This design of the first and second outlet ducts shall provide that air flowing through the curved first and/or second outlet ducts changes its direction when flowing through the curve. Thereby, larger and heavier particles hit the walls of the curved sections (inertia impaction) whereby they are broken down and/or de-agglomerated into smaller particles. Or in other words: The curved first and second outlet ducts act as a static classifier during inhalation.

It is further preferred that the first and second outlet ducts expand in direction from the first and second capsule chamber outlets to the mouthpiece portion. Preferably, the first and second outlet ducts continuously expand in direction from the first and second capsule chamber outlets to the mouthpiece portion. Thereby, according to the principle of continuity, air flowing from the capsule chamber to the mouthpiece portion is decelerated when flowing through (expanding) first and second outlet ducts.

It is further preferred that the one or more air inlet duct/s discontinuously expand/s prior to its/their connection with the at least first and second airflow paths. Thus, an inhalation airflow formed upon inhalation forms an air stream into a larger space upon exiting the air inlet duct. Due to the so-called Coanda effect, said air stream is randomly attracted to a nearby surface such that it either streams into the first or into the second airflow path. Whether the air stream flows into the first or second airflow path also depends on whether the capsule blocks one of said first or second airflow paths. If, for example, the capsule inserted into the capsule chamber blocks the second airflow path, airflow is only possible through the first airflow path and thus, said air stream will be attracted to a surface of the first airflow path. In this case, the air stream flows into the first airflow path and a reduced pressure is generated within the capsule chamber at the proximity of the first side wall due to the Venturi effect. Consequently, the capsule is moved towards the first side wall thereby inhibiting airflow through the first airflow path. Or in other words: The first airflow path is now blocked by the capsule. In this situation air can only flow through the second airflow path. If air now flows through the second airflow path and a reduced pressure is generated in the capsule chamber at the proximity of the second sidewall portion due to the Venturi effect and the capsule is now moved towards the second sidewall portion. In this situation airflow through the second airflow path is inhibited. Now, the second airflow path is (re-)closed by the capsule whereby the first airflow path is (re-)opened. Thus, the capsule itself acts as a fluidic trigger that switches the airflow from the first to the second airflow path and vice versa.

According to another preferred embodiment the inlet duct comprises a first inlet sidewall portion and a second inlet sidewall portion which taper towards an inlet opening such that a flow cross-section formed by the first and second inlet sidewall portions decreases towards the inlet opening and discontinuously expands in direction of the inhalation airflow herein after. This furthermore increases the tendency of the air to either stream into the first or into the second airflow path as described above. In detail it increases the tendency of the air to either flow along a first intermediate side wall portion which defines the first intermediate duct on its right side or alternatively flow along a second intermediate side wall portion defining the second intermediate duct on its left side. Because of the discontinuously change of the flow cross-section there are recirculating regions between the air flowing towards the capsule chamber and the intermediate side wall portions. By preferably choosing a width of a bottom wall which comprises the inlet opening in the range of 7 mm to 11 mm, preferably of 9 mm, in combination with a width of the inlet opening in the range of 0.5 mm to 5 mm, preferably of 2 mm of 2 mm there are additional small perturbations which result in a further drop in pressure of the recirculating regions and further drag the air towards an intermediate side wall portion. In other words: A ratio between a diameter of a bottom wall which comprises an inlet opening and a diameter of the inlet opening in the range of 2.2 to 14, preferably 3 to 10, more preferably of 4.5, will result in a further drop in pressure of the recirculating regions and further drag the air towards an intermediate side wall portion.

It has to be understood that the recirculating regions and the additional small perturbations will arise close to the first as well as close to the second intermediate sidewall portion when the air flows along the first airflow path or the second airflow path, respectively. Thus, as described above the air will have a tendency to flow along the first or the second airflow path until the capsule moves horizontally and blocks the corresponding first or second airflow path.

According to a preferred embodiment, the inhaler device further comprises a first inlet loop duct extending from a region within the first intermediate duct to the air inlet duct, and a second inlet loop duct extending from a region within the second intermediate duct to the air inlet duct. Said first and second inlet loop ducts have the function of guiding a part of the inhalation airflow flowing through the first or second intermediate duct to the air inlet duct such that said part of the inhalation airflow laterally impinges on the air stream formed by the inhalation airflow. If for example, the air stream formed by the inhalation airflow streams into the first airflow path, a part of said air stream flowing through the first intermediate duct is guided through the first inlet loop duct to the air inlet duct where it laterally impinges on the air stream thereby causing the air stream to switch into the second airflow path. Subsequently, a part of the air stream flowing through the second intermediate path is guided through the second inlet loop duct to the air inlet duct where it laterally impinges on the air stream thereby causing the air stream to switch back into the first airflow path. Thus, the inhalation airflow alternately flows into the first and second airflow path.

Preferably, the first and second loop ducts narrow prior to their connection with the air inlet duct.

According to a preferred embodiment, the inhaler device further comprises an outlet loop duct extending from the first capsule chamber outlet adjacent to the first sidewall portion and the first outlet duct to a second capsule chamber outlet adjacent to the second sidewall portion and the second outlet duct. The outlet loop duct has the function of guiding a part of the inhalation airflow formed upon inhalation flowing from the capsule chamber through one of the first and second outlet ducts in the direction of the mouthpiece to the other side of the capsule chamber such that said part of the inhalation airflow impinges the capsule in the proximity of its first or second end section such that the capsule is moved aside.

According to another preferred embodiment, the inhaler device further comprises a deflecting wall portion within the mouthpiece portion. The deflecting wall portion preferably extends in a direction parallel to first and second wall portions. During inhalation, larger particles hit the deflecting wall portion and are broken down/de-agglomerated into smaller particles.

According to a further preferred embodiment, the inhaler device comprises, in connection to first and second outlet ducts and the mouthpiece portion, a classifier chamber. The classifier chamber comprises a classifier chamber inlet duct and a classifier chamber outlet duct, wherein the classifier chamber inlet duct is preferably connected to first and second outlet ducts and the classifier chamber outlet duct is preferably connected to the mouthpiece portion. Preferably, when first and second outlet ducts are curved and connected to form one continuous curve, the classifier chamber inlet duct is connected to the apex of the continuous curve formed by the first and second outlet ducts. The classifier chamber further comprises a classifier chamber deflecting wall portion extending in a direction parallel to first and second wall portions and first and second classifier ducts extending between the classifier chamber inlet duct and the classifier chamber outlet duct. Preferably, first and second classifier ducts are curved and connected to form one continuous curve, where the mouthpiece portion is connected to the apex of the curve formed by the first and second classifier ducts. During inhalation, larger particles hit the deflecting wall portion and are broken down/de-agglomerated into smaller particles. Subsequently, larger and heavier particles still remaining in the inhalation airflow hit the walls of the curved section (inertia impaction) whereby they are broken down and/or de-agglomerated into smaller particles.

The above objects are further achieved by a method of delivering a dose of medicament in dry powder form from a capsule to a patient in need thereof. In a first step, a capsule having a longitudinal axis and first and second end sections which contains a dose of medicament in dry powder form is provided.

Furthermore, an inventive inhaler device is provided and the capsule is inserted into the capsule chamber of the inhaler device.

Subsequently, openings are pierced at the first and second end sections of the capsule using movable piercing means. Preferably, said moveable piercing means are located in the first and second sidewalls of the capsule chamber.

After piercing the openings into the first and second end sections of the capsule, the patient inhales through the mouthpiece portion such that an inhalation airflow is formed. The inhalation airflow flows through the one or more air inlet ducts via the capsule chamber and the mouthpiece portion into the patient's lungs. Upon inhalation, the capsule located in the capsule chamber performs an oscillating movement in the capsule chamber parallel to its longitudinal axis between the first and the second sidewall portions when an airflow is initiated through the first and the second airflow paths in a direction from the at least one air inlet duct towards the mouthpiece portion.

The capsule to be inserted into the inhaler according to the present invention is preferably made of gelatin, HPMC, aluminium and/or any other material which can hold the dry powder and which can be pierced or slit to open.

DETAILED DESCRIPTION OF THE INVENTION

The invention is further described by referring to the appended figures which show preferred embodiments and shall by no means limit the present invention.

Figure 1:
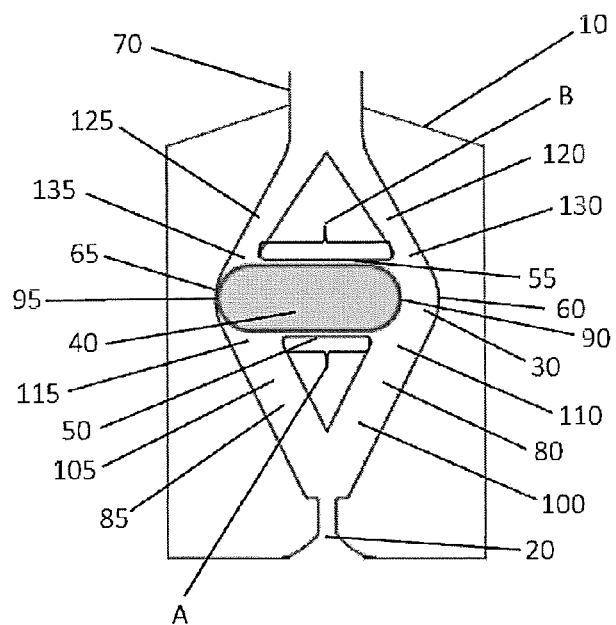
FIG. 1 shows a schematic view of an embodiment of an inhaler according to the present invention together with a capsule inserted in the capsule chamber.

With reference to FIG. 1, a first exemplary embodiment of an inhaler device according to the present invention will be described.

The inhaler comprises an inhaler housing 10 comprising one air inlet duct 20 through which ambient air flows into the inhaler device during inhalation. The inhaler further comprises an elongated capsule chamber 30 adapted for receiving a capsule 40 containing a dose of medicament in dry powder form. FIG. 1 shows an embodiment of the inventive inhaler device together with a capsule 40 inserted in the capsule chamber 30. The capsule 40 has a longitudinal axis and first and second end sections 90, 95 delimiting the capsule 40 on opposing ends. The capsule 40 further comprises a central, cylindrical section between said first and second end sections 90, 95.

The capsule chamber 30 has a longitudinal axis and is defined by a wall arrangement including a first and a second supporting wall portion 50, 55 opposing each other in a direction perpendicular to the longitudinal axis. As shown in FIG. 1, first and second supporting wall portions 50, 55 are arranged parallel to each other. The first supporting wall portion 50 has an extension in a direction extending parallel to the longitudinal axis of the capsule chamber 30 with a length "A" and the second supporting wall portion 55 has an extension in a direction extending parallel to the longitudinal axis of the capsule chamber 30 with a length "B". In the embodiment shown in FIG. 1, "B" is larger than "A".

The wall arrangement further includes first and second sidewall portions 60, 65 opposing each other in the direction of the longitudinal axis of the capsule chamber 30.

The inhaler device further comprises a mouthpiece portion 70 through which the medicament in dry powder form is dispensable.

Moreover, the embodiment of the inventive inhaler device shown in FIG. 1 comprises at least first and second airflow paths 80, 85 which extend between the at least one air inlet duct 20, the capsule chamber 30 and the mouthpiece portion 70 to enable an inhalation airflow formed upon inhalation to flow through the air inlet duct 20 via the capsule chamber 30 and the mouthpiece portion 70.

The first airflow path 80 comprises a first intermediate duct 100 extending from the one air inlet duct 20 to a first capsule chamber inlet 110 adjacent to the first sidewall portion 60 and a first outlet duct 120 extending from a first capsule chamber outlet 130 adjacent to the first sidewall portion 60 to the mouthpiece portion 70. The second airflow path 85 comprises a second intermediate duct 105 extending from the air inlet duct 20 to a second capsule chamber inlet 115 adjacent to the second sidewall portion 65, and a second outlet duct 125 extending from a second capsule chamber outlet 135 adjacent to the second sidewall portion 65 to the mouthpiece portion 70.

Said first and second outlet ducts 120, 125 expand in direction from the first and second capsule chamber outlets 130, 135 to the mouthpiece portion 70.

The first capsule chamber inlet 110 is formed between the first supporting wall portion 50 and the first sidewall portion 60. The second capsule chamber inlet 115 is formed between the first supporting wall portion 50 and the second sidewall portion 65. The first capsule chamber outlet 130 is formed between the second supporting wall portion 55 and the first sidewall portion 60. The second capsule chamber outlet 135 is formed between the second supporting wall portion 55 and the second sidewall portion 65.

In the embodiment shown in FIG. 1, the size of the first capsule chamber inlet 110 is identical to the size of the second capsule chamber inlet 115 and the size of the first capsule chamber outlet 130 is identical to the size of the second capsule chamber outlet 135. The size of said first and second capsule chamber inlets 110, 115 is larger than the size of said first and second capsule chamber outlets 130, 135.

The capsule 40 inserted into the capsule chamber 30 has an extension between its first and second end sections 90, 95 that is larger than the size of the first and second capsule chamber inlets 110. In particular, the capsule 40 inserted into the capsule chamber 30 has an extension between its first and second end sections that is larger than the sum of length "B" and the size of the first or second capsule chamber outlet 130, 135. In this way, the capsule 40 acts as an airflow barrier preventing air to flow from the first airflow path 80 to the second airflow path 85 (or vice versa) within the capsule chamber 30. Additionally, a constriction zone is created within the capsule chamber 30 between the first or second sidewall portion 60, 65 and the first or second end section 90, 95 of the capsule 40. FIG. 1 shows a situation where the capsule blocks the second airflow path 85 and creates a constriction zone between the first end section 90 of the capsule 40 and the first sidewall portion 60.

Furthermore, the embodiment shown in FIG. 1 comprises an air inlet duct 20 that abruptly expands prior to its connection with the at least first and second airflow paths 80, 85.

During inhalation, an inhalation airflow is formed within the inhaler device. The inhalation airflow forms an air stream into a larger space upon exiting the air inlet duct 20. As the second airflow path 85 is blocked by the capsule 40, said air stream flows into the first airflow path 80. According to the principle of continuity, the inhalation airflow has an increased velocity when flowing through the constriction zone formed between the first end section 90 of the capsule 40 and the first sidewall portion 60. According to the principle of conservation of mechanical energy, said gain in kinetic energy—due to the increased velocity of the air flowing through the constriction zone—leads to a drop in pressure in the capsule chamber 30 at the proximity of the first sidewall portion 60 (Venturi effect). Consequently, due to the reduced pressure in the capsule chamber 30 at the proximity of the first sidewall portion 60, the capsule 40 is moved towards the first sidewall portion 60. Subsequently, after being moved to the first sidewall portion 60, the capsule 40 blocks the first airflow path 80. At the same time, the second airflow path 85 is opened. The capsule 40 now forms a constriction zone within the capsule chamber 30 between the second end section 95 of the capsule 40 and the second sidewall portion 65. Now, as the first airflow path 80 is blocked by the capsule 40, the inhalation airflow stream into the second airflow path 85 thereby creating a reduced pressure inside the capsule chamber 30 when flowing through the constriction zone. Thus, the capsule 40 is moved to the second sidewall portion 65 thereby (re-)opening the first airflow path 80 and (re-)closing the second airflow path 85. In this way, the capsule 40 performs an oscillating movement in the capsule chamber 30 parallel to its longitudinal axis between the first and second sidewall portions 60, 65 when an airflow is initiated through the first and the second airflow paths 80, 85 in a direction from the air inlet duct 20 towards the mouthpiece portion 70. While performing the oscillating movement, impacts between the capsule 40, in particular its first and second end sections 90, 95, and the first and second sidewall portions 60, 65 of the capsule chamber 30 are generated such that a dose of medicament in dry powder form contained within the capsule 40 is broken down into fine, breathable fractions and finely dispersed inside the capsule 40. The finely dispersed powder exits the capsule 40 through holes in the first and second end sections 90, 95, is entrained in the inhalation airflow dispensed through the mouthpiece portion 70.

Figure 2:
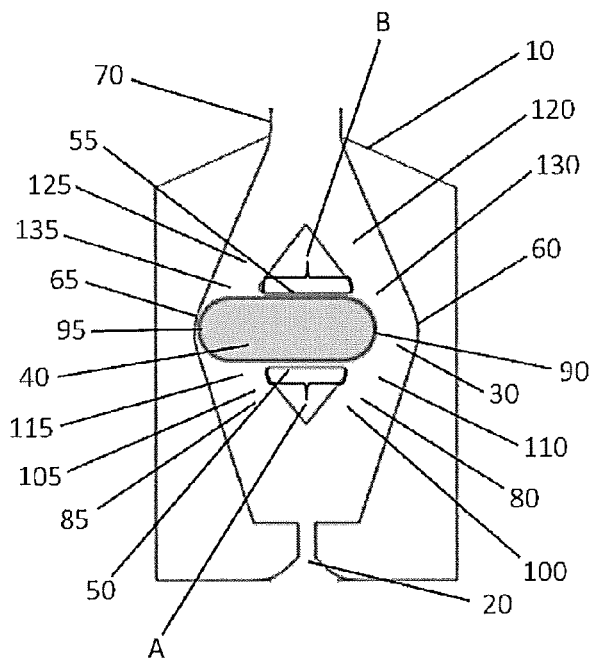
FIG. 2 shows a schematic view of another embodiment of an inhaler according to the present invention together with a capsule inserted in the capsule chamber.

With reference to FIG. 2, a second exemplary embodiment of an inhaler device according to the present invention is described. Also FIG. 2 shows an embodiment of the inventive inhaler device together with a capsule 40 inserted into the capsule chamber 30.

This embodiment of the inventive inhaler device corresponds to the embodiment shown in FIG. 1 with the first and second airflow paths 80, 85 being broader. Or in other words: The first and second airflow paths 80, 85 have a larger flow cross-section. Furthermore, the first and second intermediate ducts 100, 105 taper in direction from the at least one air inlet duct 20 to the first and second capsule chamber inlets 110, 115 such that air flowing from the at least one air inlet duct to the capsule chamber 30 is accelerated when flowing through first and second intermediate ducts 100, 105.

Figure 3:
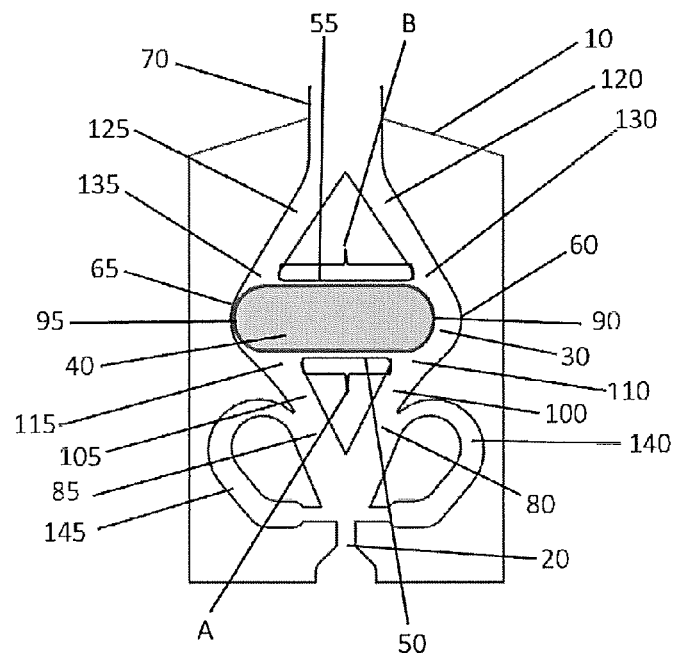
FIG. 3 shows a schematic view of an embodiment of an inhaler according to the present invention comprising a first and a second inlet loop duct together with a capsule inserted in the capsule chamber.

With reference to FIG. 3, a further exemplary embodiment of an inhaler device according to the present invention is described. Also FIG. 3 shows an embodiment of the inventive inhaler device together with a capsule 40 inserted into the capsule chamber 30.

The inhaler comprises an inhaler housing 10 comprising one air inlet duct 20 through which ambient air flows into the inhaler device during inhalation. The inhaler further comprises an elongated capsule chamber 30 adapted for receiving a capsule containing a dose of medicament in dry powder form. The capsule 40 has a longitudinal axis and first and second end sections 90, 95 delimiting the capsule 40 on opposing ends. The capsule 40 further comprises a central, cylindrical section between said first and second end sections 90, 95.

The capsule chamber 30 has a longitudinal axis and is defined by a wall arrangement including a first and a second supporting wall portions 50, 55 opposing each other in a direction perpendicular to the longitudinal axis of the capsule chamber. The first supporting wall portion 50 has an extension in a direction extending parallel to the longitudinal axis of the capsule chamber 30 with a length "A" and the second supporting wall portion 55 has an extension in a direction extending parallel to the longitudinal axis of the capsule chamber 30 with a length "B". In the embodiment shown in FIG. 3, "B" is larger than "A".

The wall arrangement further includes first and second sidewall portions 60, 65 opposing each other in the direction of the longitudinal axis of the capsule chamber.

The inhaler device further comprises a mouthpiece portion 70 through which the medicament in dry powder form is dispensable.

Moreover, the embodiment of the inventive inhaler device shown in FIG. 3 comprises at least first and second airflow paths 80, 85 which extend between the at least one air inlet duct 20, the capsule chamber 30 and the mouthpiece portion 70 to enable an inhalation airflow formed upon inhalation to flow through the at least one air inlet duct 20 via the capsule chamber 30 and the mouthpiece portion 70.

The first airflow path 80 comprises a first intermediate duct 100 extending from the at least one air inlet duct 20 to a first capsule chamber inlet 110 adjacent to the first sidewall portion 60 and a first outlet duct 120 extending from a first capsule chamber outlet 130 adjacent to the first sidewall portion 60 to the mouthpiece portion 70. The second airflow path 85 comprises a second intermediate duct 105 extending from the at least one air inlet duct 20 to a second capsule chamber inlet 115 adjacent to the second side wall 65, and a second outlet duct 125 extending from a second capsule chamber outlet 135 adjacent to the second sidewall 65 to the mouthpiece portion 70.

The first capsule chamber inlet 110 is formed between the first supporting wall portion 50 and the first sidewall portion 60. The second capsule chamber inlet 115 is formed between the first supporting wall portion 50 and the second sidewall portion 65. The first capsule chamber outlet 130 is formed between the second supporting wall portion 55 and the first sidewall portion 60. The second capsule chamber outlet 135 is formed between the second supporting wall portion 55 and the second sidewall portion 65.

The size of the first capsule chamber inlet 110 is identical to the size of the second capsule chamber inlet 115 and the size of the first capsule chamber outlet 130 is identical to the size of the second capsule chamber outlet 135. The size of said first and second capsule chamber inlets 110, 115 is larger than the size of said first and second capsule chamber outlets 130, 135.

The capsule 40 inserted into the capsule chamber 30 has an extension between its first and second end sections 90, 95 that is larger than the size of the first and second capsule chamber inlets 110, 115. In particular, the capsule 40 inserted into the capsule chamber 30 has an extension between its first and second end sections 90, 95 that is larger than the sum of the length "B" and the size of the first or second capsule chamber outlet 130, 135. In this way, the capsule 40 acts as an airflow barrier preventing air to flow from the first airflow path 80 to the second airflow path 85 (or vice versa) within the capsule chamber 30. Furthermore, a constriction zone is created within the capsule chamber 30 between the first or second sidewall portion 60, 65 and the first or second end section 90, 95 of the capsule 40. FIG. 1 shows a situation where the capsule 40 blocks the second airflow path 850 and creates a constriction zone between the first end section 90 of the capsule 40 and the first sidewall portion 60.

Furthermore, the air inlet duct 20 abruptly expands prior to its connection with the at least first and second airflow paths 80, 85 such that an inhalation airflow formed upon inhalation forms air stream into a larger space upon exiting the air inlet duct 20.

Moreover, the embodiment shown in FIG. 3 comprises a first inlet loop duct 140 extending from a region within the first intermediate duct 100 to the air inlet duct 20, and a second inlet loop duct 145 extending from a region within the second intermediate duct 105 to the air inlet duct 20 for guiding a part of the inhalation airflow flowing through the first or second intermediate duct 100, 105 to the air inlet duct 20 such that said part of the inhalation airflow laterally impinges on the air stream formed by the inhalation airflow. The first and second loop ducts 140, 145 narrow prior to their connection with the air inlet duct 20.

During inhalation, an inhalation airflow is formed within the inhaler device. The inhalation airflow forms an air stream into a larger space upon exiting the air inlet duct 20. As the second airflow path 85 is blocked by the capsule (see FIG. 3), said air stream flows into the first airflow path 80. According to the principle of continuity, the inhalation airflow has an increased velocity when flowing through the constriction zone formed between the first end section 90 of the capsule 40 and the first sidewall portion 60. According to the principle of conservation of mechanical energy, said gain in kinetic energy—due to the increased velocity of the air flowing through the constriction zone—leads to a drop in pressure in the capsule chamber 30 at the proximity of the first sidewall portion 60 (Venturi effect). Consequently, due to the reduced pressure in the capsule chamber 30 at the proximity of the first sidewall portion 60, the capsule 40 is moved towards the first sidewall portion 60. Now, a constriction is created between the second end section 95 of the capsule 40 and the second sidewall portion 65. Additionally, a part of said air stream flowing through the first intermediate duct 100 is guided through the first inlet loop duct 140 to the air inlet duct 20 where it laterally impinges on the air stream thereby causing the air stream to switch into the second airflow path 85. Subsequently, the air stream flows into the second airflow path 85 and through the constriction between the second end section 95 of the capsule 40 and the second sidewall portion 65 causing a drop in pressure in the capsule chamber 30 at the proximity of the second sidewall portion 65 due to the Venturi effect. Consequently, the capsule 40 is moved towards the second sidewall portion 65. Additionally, a part of said air stream flowing through the second intermediate duct 105 is guided through the second inlet loop duct 145 to the air inlet duct 20 where it laterally impinges on the air stream thereby causing the air stream to switch into the first airflow path 80. In this way, the inhalation airflow alternately flows into the first and second airflow path 80, 85 thereby causing the capsule 40 to perform an oscillating movement between the first and second sidewall portions 60, 65 of the capsule chamber 30.

Figure 4:
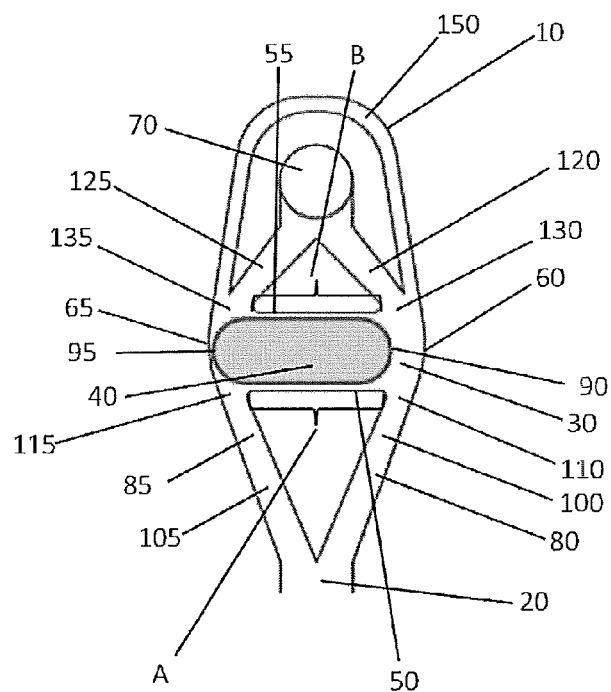
FIG. 4 shows a schematic view of an embodiment of an inhaler according to the present invention comprising an outlet loop duct together with a capsule inserted in the capsule chamber.

With reference to FIG. 4, a further exemplary embodiment of an inhaler device according to the present invention is described. Also FIG. 4 shows an embodiment of the inventive inhaler device together with a capsule 40 inserted into the capsule chamber 30.

The inhaler comprises an inhaler housing 10 comprising one air inlet duct 20 through which ambient air flows into the inhaler device during inhalation. The inhaler further comprises an elongated capsule chamber 30 adapted for receiving a capsule containing a dose of medicament in dry powder form. The capsule 40 has a longitudinal axis and first and second end sections 90, 95 delimiting the capsule 40 on opposing ends. The capsule 40 further comprises a central, cylindrical section between said first and second end sections 90, 95.

The capsule chamber 30 has a longitudinal axis and is defined by a wall arrangement including a first and a second supporting wall portion 50, 55 opposing each other in a direction perpendicular to the longitudinal axis of the capsule chamber 30. The first supporting wall portion 50 has an extension in a direction extending parallel to the longitudinal axis of the capsule chamber 30 with a length "A" and the second supporting wall portion 55 has an extension in a direction extending parallel to the longitudinal axis of the capsule chamber 30 with a length "B". In the embodiment shown in FIG. 4, "A" is larger than "B".

The wall arrangement further includes first and second sidewall portions 60, 65 opposing each other in the direction of the longitudinal axis of the capsule chamber.

The inhaler device further comprises a mouthpiece portion 70 through which the medicament in dry powder form is dispensable.

Moreover, the embodiment of the inventive inhaler device shown in FIG. 4 comprises at least first and second airflow paths 80, 85 which extend between the air inlet duct 20, the capsule chamber 30 and the mouthpiece portion 70 to enable an inhalation airflow formed upon inhalation to flow through the air inlet duct 20 via the capsule chamber 30 and the mouthpiece portion 70.

The first airflow path 80 comprises a first intermediate duct 100 extending from the air inlet duct 20 to a first capsule chamber inlet 110 adjacent to the first side wall 60 and a first outlet duct 120 extending from a first capsule chamber outlet 130 adjacent to the first sidewall 60 to the mouthpiece portion 70. The second airflow path 85 comprises a second intermediate duct 105 extending from the at least one air inlet duct 20 to a second capsule chamber inlet 115 adjacent to the second side wall 65, and a second outlet duct 125 extending from a second capsule chamber outlet 135 adjacent to the second sidewall 65 to the mouthpiece portion 70.

The first capsule chamber inlet 110 is formed between the first supporting wall portion 50 and the first sidewall portion 60. The second capsule chamber inlet 115 is formed between the first supporting wall portion 50 and the second sidewall portion 65. The first capsule chamber outlet 130 is formed between the second supporting wall portion 55 and the first sidewall portion 60. The second capsule chamber outlet 135 is formed between the second supporting wall portion 55 and the second sidewall portion 65.

The size of the first capsule chamber inlet 110 is identical to the size of the second capsule chamber inlet 115 and the size of the first capsule chamber outlet 130 is identical to the size of the second capsule chamber outlet 135. The size of said first and second capsule chamber inlets 110, 115 is smaller than the size of said first and second capsule chamber outlets 130, 135.

The capsule 40 inserted into the capsule chamber 30 has an extension between its first and second end sections 90, 95 that is larger than the size of the first and second capsule chamber outlets 130, 135. In particular, the capsule 40 inserted into the capsule chamber 30 has an extension between its first and second end sections 90, 95 that is larger than the sum of length "A" and the size of the first or second capsule chamber inlet 110, 115. In this way, the capsule 40 acts as an airflow barrier preventing air to flow from the first airflow path 80 to the second airflow path 85 (or vice versa) within the capsule chamber 30.

The inhaler device further comprises an outlet loop duct 150 extending from the first capsule chamber outlet 130 adjacent to the first sidewall portion 60 and the first outlet duct 120 to a second capsule chamber outlet 135 adjacent to the second sidewall portion 65 and the second outlet duct 125. The outlet loop duct 150 has the function of guiding a part of the inhalation airflow formed upon inhalation flowing from the capsule chamber 30 through one of the first and second outlet ducts 120, 125 in the direction of the mouthpiece portion 70 to the other side of the capsule chamber 30 such that said part of the inhalation airflow impinges the capsule 40 in the proximity of its first or second end section 90, 95 such that the capsule 40 is pushed aside.

During inhalation, an inhalation airflow is formed within the inhaler device. FIG. 4 shows a situation where the second airflow path 85 is blocked by the capsule 40. Thus, the inhalation airflow flows into and through the first airflow path 80. A part of said airflow flowing through the first outlet duct 120 is guided through the outlet loop duct 150 to the second capsule chamber outlet 130 such that it impinges the capsule 40 at the in the proximity of its second end section 95 such that the capsule 40 is pushed in the direction of the first sidewall portion 60 thereby opening the second airflow path 85 and closing the first airflow path 80. Subsequently, the inhalation airflow flows into and through the second airflow path 85. A part of said airflow flowing through the second outlet duct 125 is guided through the outlet loop duct 150 to the first capsule chamber outlet 130 such that it impinges the capsule 40 at the in the proximity of its first end section 90 such that the capsule 40 is pushed in the direction of the second sidewall portion 65 thereby (re-)opening the second airflow 85 path and (re-)closing the first airflow path 80. In this way, the inhalation airflow alternately flows into the first and second airflow path 80, 85 causing the capsule 40 to perform an oscillating movement between the first and second sidewall portions 60, 65 of the capsule chamber 30.

Figure 5:
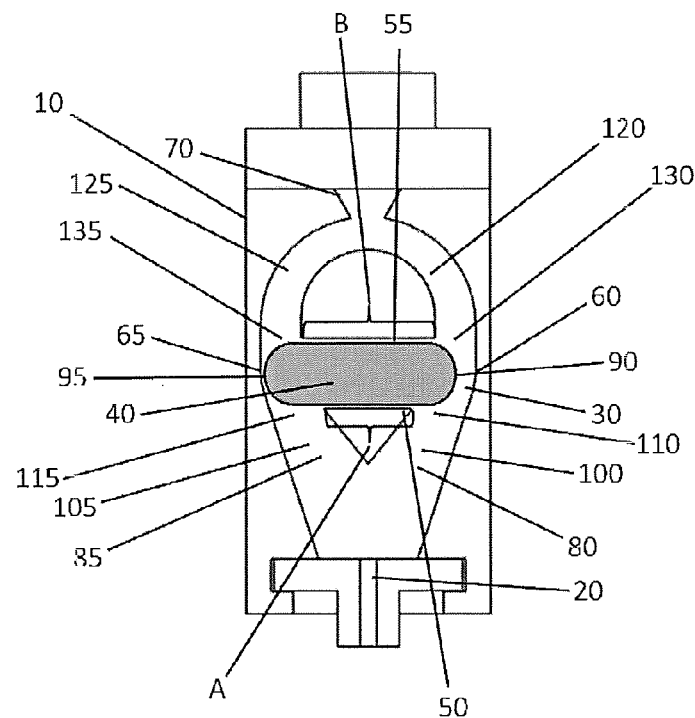
FIG. 5 shows a schematic view of an embodiment of an inhaler according to the present invention comprising curved first and second outlet ducts together with a capsule inserted in the capsule chamber.

With reference to FIG. 5 a further embodiment of an inhaler device according to the present invention will be described. Also FIG. 5 shows an embodiment of the inventive inhaler device together with a capsule 40 inserted into the capsule chamber 30.

This embodiment basically corresponds to the embodiment shown in FIG. 2 with the first and second outlet ducts 120, 125 being curved and connected to form one continuous curve. The mouthpiece portion 70 is connected to the apex of the continuous curve formed by the first and second outlet ducts 120, 125.

Thus, during inhalation, air flowing through the curved first and second outlet ducts 120, 125 changes its direction when flowing through the curve and thereby, larger and heavier particles hit the (outer) wall of the curved sections (inertia impaction) whereby they are broken down and/or de-agglomerated into smaller particles. Or in other words: The curved first and second outlet ducts 120, 125 act as a static classifier during inhalation.

Figure 6:
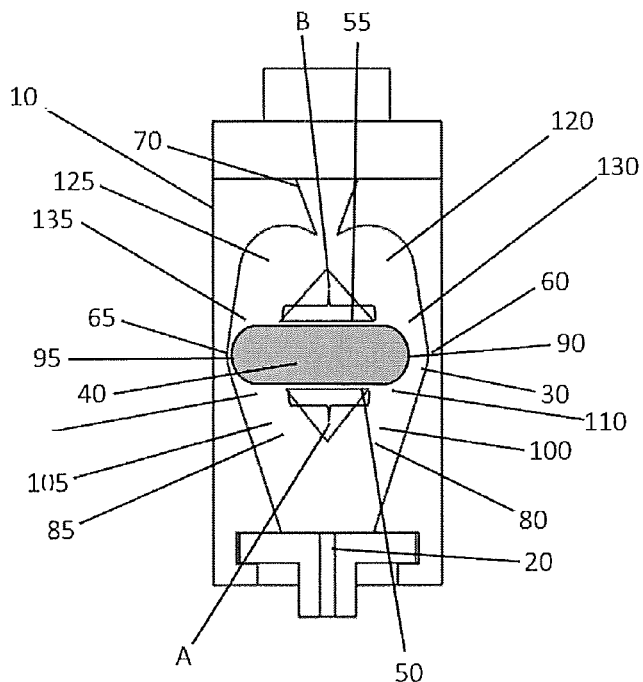
FIG. 6 shows a schematic view of another embodiment of an inhaler according to the present invention comprising curved first and second outlet ducts together with a capsule inserted in the capsule chamber.

With reference to FIG. 6 a further exemplary embodiment of an inhaler device according to the present invention is described. Also FIG. 6 shows an embodiment of the inventive inhaler device together with a capsule 40 inserted into the capsule chamber 30.

This embodiment of the inventive inhaler device basically corresponds to the embodiment shown in FIG. 5. Like the embodiment shown in FIG. 5 first and second outlet ducts 120, 125 are curved and connected. Also in this embodiment the first and second outlet ducts 120, 125 act as a static classifier during inhalation. The first and second outlet ducts 120, 125 have a larger flow cross-section (or diameter) than the first and second outlet ducts 120, 125 of the embodiment shown in FIG. 5.

Figure 7:
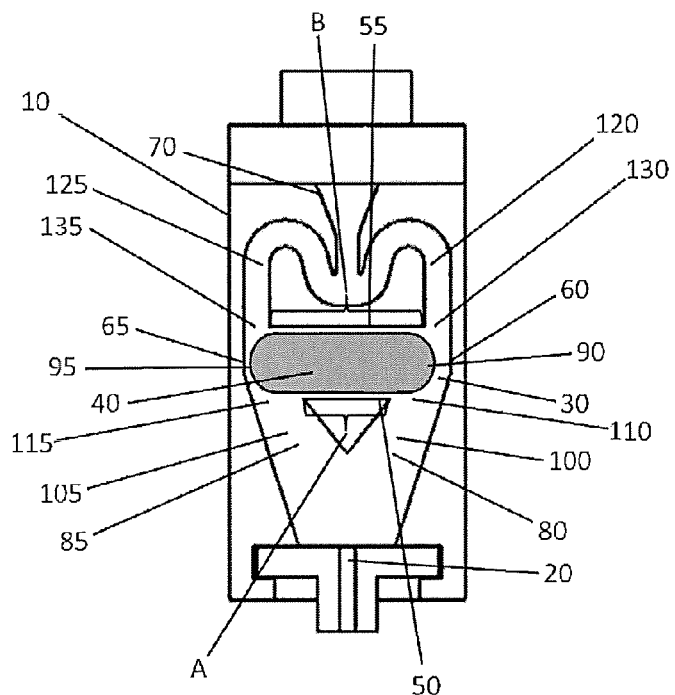
FIG. 7 shows a schematic view of a further embodiment of an inhaler according to the present invention comprising curved first and second outlet ducts together with a capsule inserted in the capsule chamber.

With reference to FIG. 7 a further exemplary embodiment of an inhaler device according to the present invention is described. Also FIG. 7 shows an embodiment of the inventive inhaler device together with a capsule 40 inserted into the capsule chamber 30.

The embodiment shown in FIG. 7 basically corresponds to the embodiment shown in FIG. 2 with the first and second outlet ducts 120, 125 being curved and connected to form a wavy form comprising two crests and one trough. Also in this embodiment the first and second outlet ducts 120, 125 act as a static classifier during inhalation. The mouthpiece portion 70 is connected to the trough.

Thus, during inhalation, air flowing through the curved first and second outlet ducts 120, 125 changes its direction when flowing through the curve and thereby, larger and heavier particles hit the (outer) wall of the curved sections (inertia impaction) whereby they are broken down and/or de-agglomerated into smaller particles.

Figure 8:
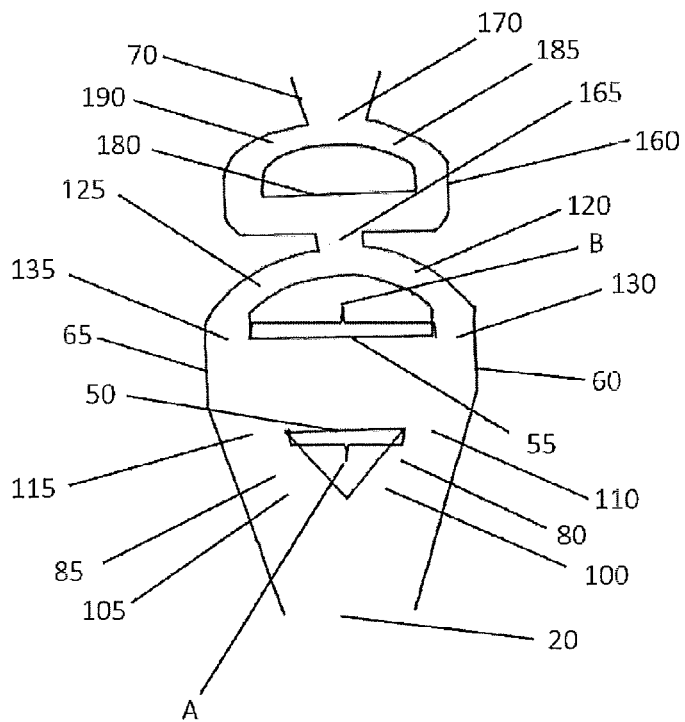
FIG. 8 shows a schematic view of an embodiment of an inhaler according to the present invention comprising a deflecting wall portion within the mouthpiece portion.

With reference to FIG. 8, a further embodiment of the inhaler device according to the present invention is described. The embodiment shown in FIG. 8 basically corresponds to the embodiment shown in FIG. 5 with a deflecting wall portion 155 being present within the mouthpiece portion 70. The deflecting wall portion 155 extends in a direction parallel to first and second wall portions 50, 55.

Figure 9:
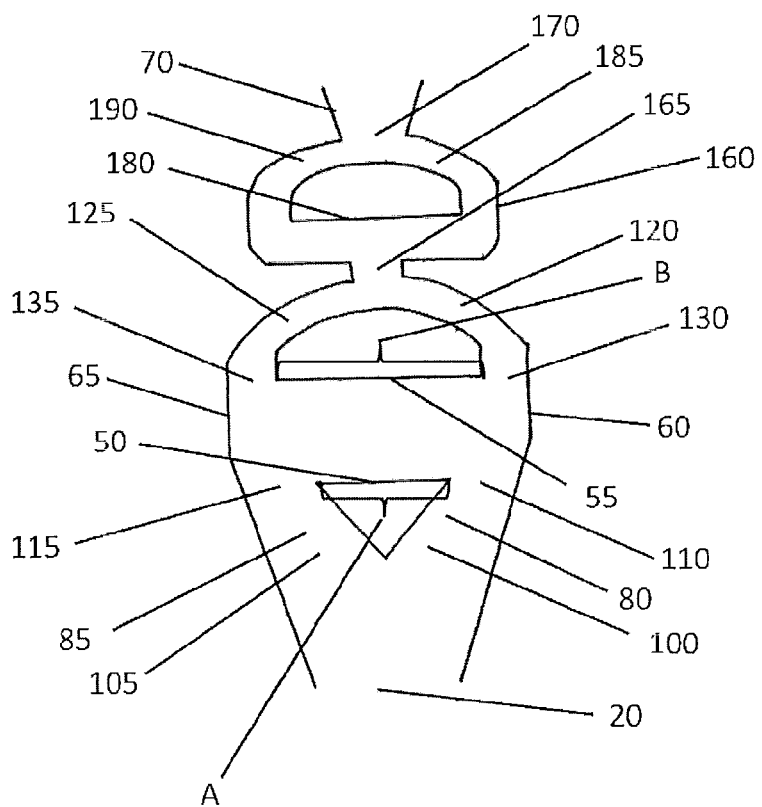
FIG. 9 shows a schematic view of an embodiment of an inhaler according to the present invention comprising a classifier chamber.

With reference to FIG. 9, another embodiment of the inhaler device according to the present is described. The embodiment shown in FIG. 9 basically corresponds to the embodiment shown in FIG. 5 with a classifier chamber 160 being present in connection with first and second outlet ducts 120, 125 and the mouthpiece portion 70. The classifier chamber 160 comprises a classifier chamber inlet duct 165 and a classifier chamber outlet duct 170, wherein the classifier chamber inlet duct 165 is in connection with the apex of the curve formed by the first and second outlet ducts 120, 125 and the classifier chamber outlet duct 175 is in connection with the mouthpiece portion 70. The classifier chamber further comprises a classifier chamber deflecting wall portion 180 extending in a direction parallel to first and second wall portions 50, 55. The classifier chamber 160 further comprises curved first and second classifier ducts 185, 190 extending between the classifier chamber inlet duct 165 and the classifier chamber outlet 170 duct. The first and second classifier ducts 170, 175 are curved and connected to form one continuous curve, where the mouthpiece portion 70 is connected to the apex of the curve formed by the first and second classifier ducts 170, 175.

Figure 10:
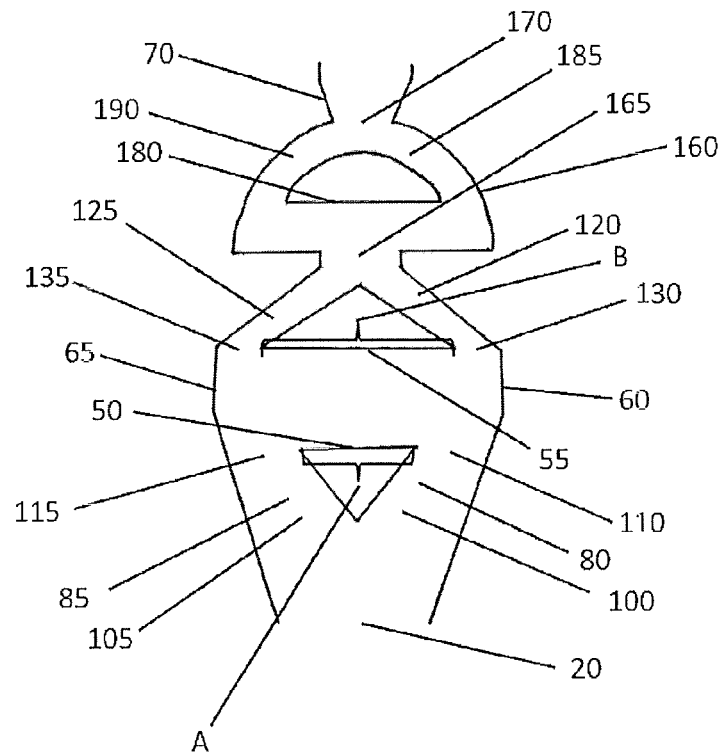
FIG. 10 shows a schematic view of another embodiment of an inhaler according to the present invention comprising a classifier chamber.
Figure 11:
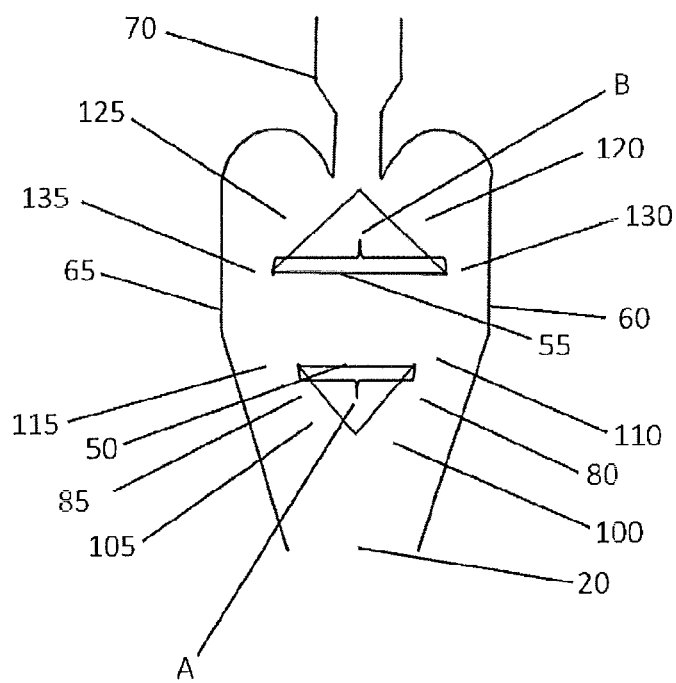
FIG. 11 shows a further example of an embodiment of an inhaler according to the present invention.
Figure 12:
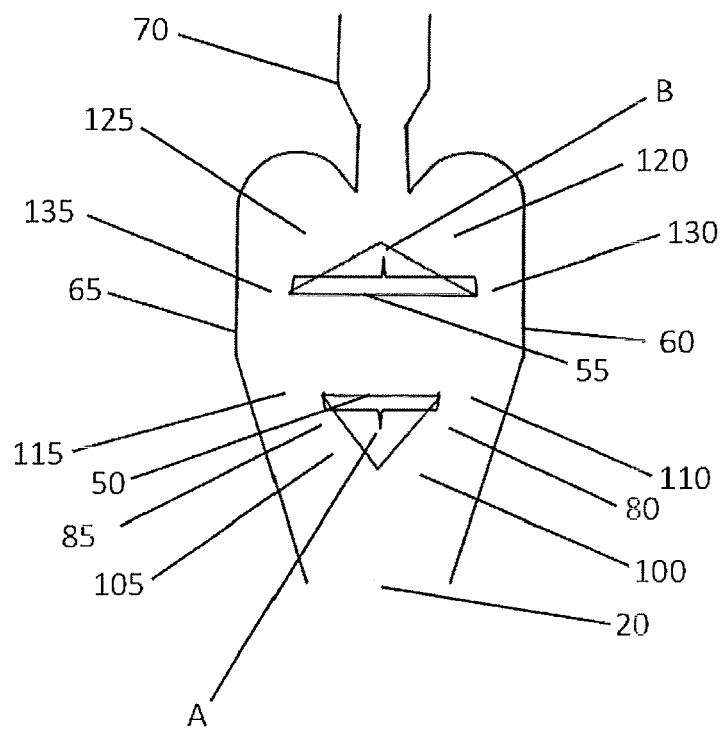
FIG. 12 shows another example of an embodiment of an inhaler according to the present invention.
Figure 13:
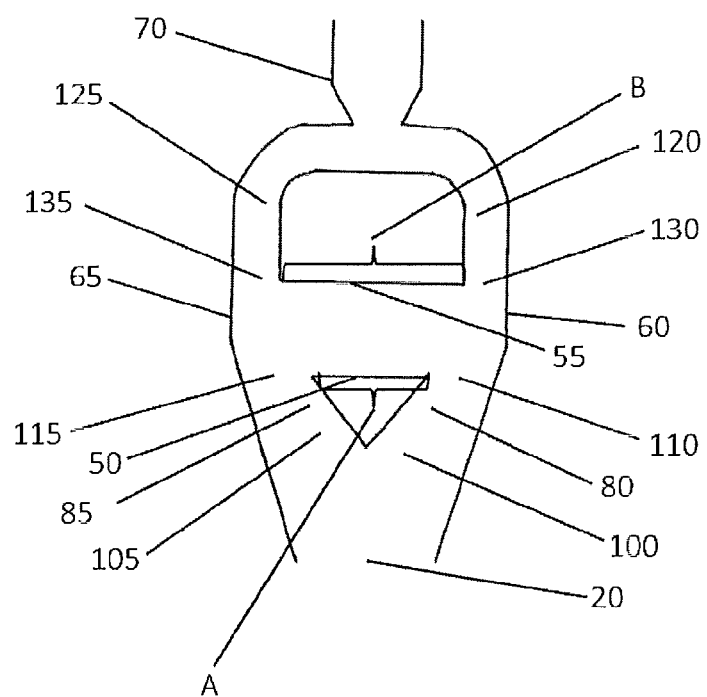
FIG. 13 shows another example of an embodiment of an inhaler according to the present invention.
Figure 14:
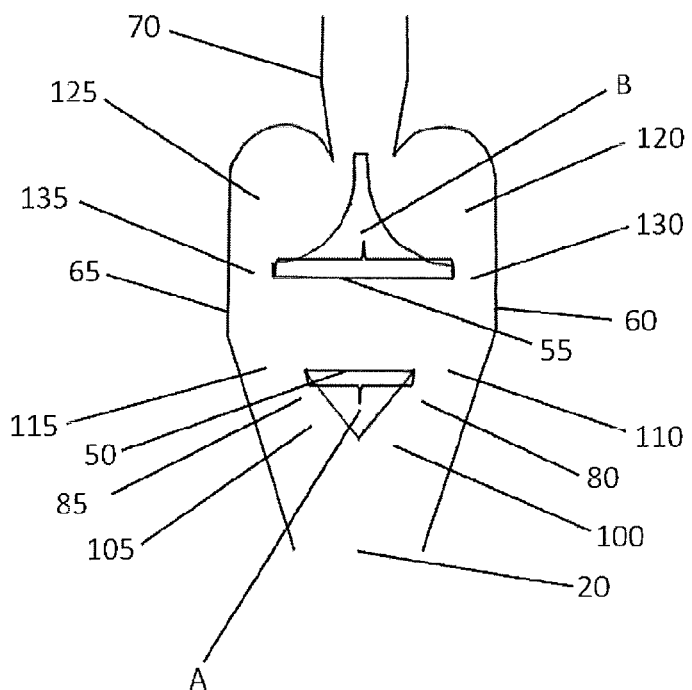
FIG. 14 shows another example of an embodiment of an inhaler according to the present invention.

FIG. 10 shows a further embodiment of an inhaler according to the present invention comprising a classifier chamber 160 with a slightly different geometry than the classifier chamber 160 shown in the embodiment shown in FIG. 9.

FIGS. 11 to 16 show further embodiments of an inhaler according to the present invention.

Figure 15:
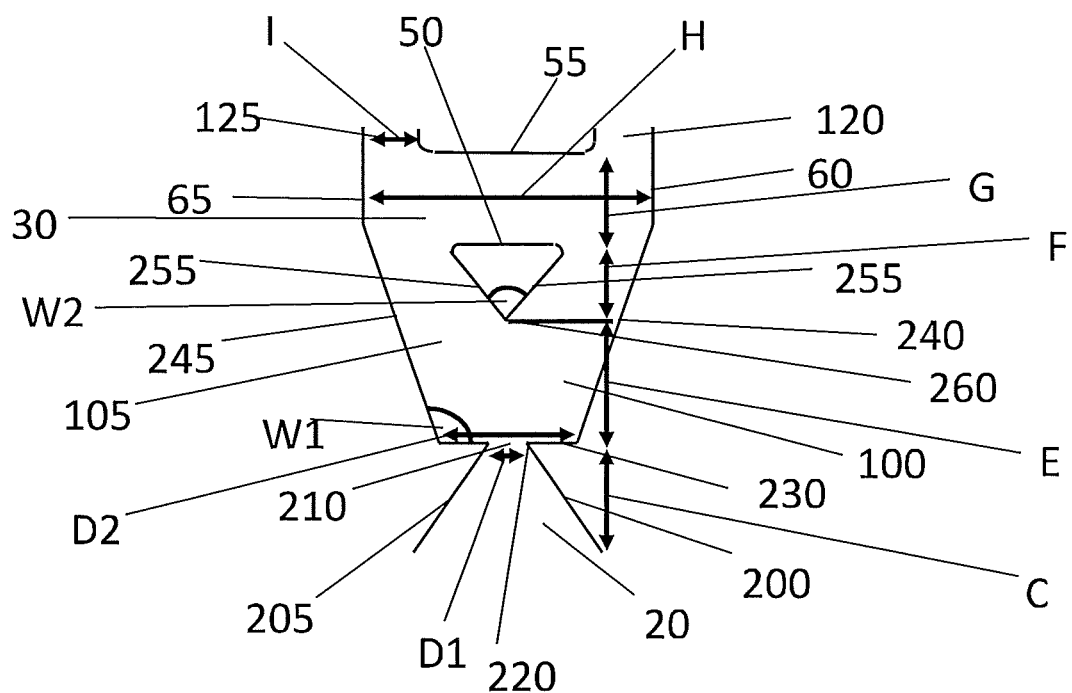
FIG. 15 shows a schematic view of a further embodiment of an inhaler according to the present invention.
Figure 16:
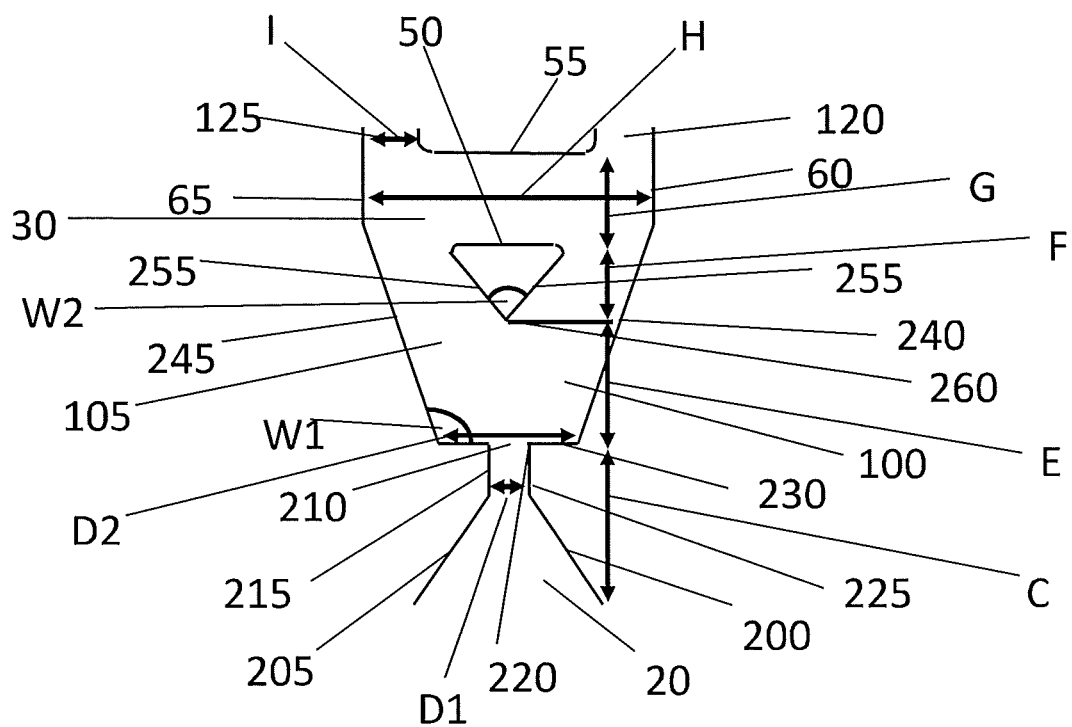
FIG. 16 shows a schematic view of a still further embodiment of an inhaler according to the present invention.

FIGS. 15 and 16 show further embodiments of the inhaler device. These embodiments differ from the one shown in FIG. 2 by the shape of the inlet duct 20 through which ambient air flows into the inhaler device during inhalation.

In both embodiments, the inlet duct 20 comprises a first inlet sidewall portion 200 and a second inlet sidewall portion 205 which taper towards an inlet opening 210. The inlet opening 210 is defined at the point where the first and second inlet sidewall portions 200, 205 cease to converge towards each other and either converge with a bottom wall 230 in the case of FIG. 15, or converge with parallel walls 215 and 225 in the case of FIG. 16. The parallel walls 215 and 225 then extend to and converge with a bottom wall 230.

A flow cross-section formed by the first and second inlet sidewall portions 200, 205 decreases towards the inlet opening 210, and in the case of FIG. 15, abruptly expands herein after 220. In the case of FIG. 16, the flow cross-section formed by the first and second inlet sidewall portions 200, 205 decreases towards the inlet opening 210, following which it is maintained along 215 and 225 before then abruptly expanding 220.

The abrupt change in cross-section and expansion encourages the inhaled air to form a jet as it enters the first intermediate duct. As a jet, the inhaled air will have a tendency to either flow along a first intermediate side wall portion 240 which defines the first intermediate duct 100 on its right side or alternatively to flow along a second intermediate side wall portion 245 defining the second intermediate duct 105 on its left side. The jet can then be encouraged to switch between the ducts 100 and 105 by the presence of natural jetflow instabili-ties, downs-stream blockage from the capsule, or a deliberate pressure pulse targeted laterally at the jet as provided by extra channels similar to those shown in FIGS. 3, 140 and 145.

The first intermediate side wall portion 240 runs from the bottom wall 230 towards the first sidewall portion 60. Analogously the second intermediate side wall portion 245 runs from the bottom wall 230 towards the second sidewall portion 65.

A vertical distance C between the lowermost end of the first and second inlet sidewall portions 200, 205 and the bottom wall 230 comprising the inlet opening 210 is preferably in the range of 5 mm to 10 mm, more preferably about 7 mm. The inlet opening 210 preferably has a width D1 in the range of 0.5 mm to 5 mm, more preferably of about 2 mm. The bottom wall 230 preferably has a width D2 in the range of 7 mm to 11 mm, more preferably of about 9 mm. The first and second intermediate sidewall portions 240, 245 and the bottom wall 230 preferably enclose an angle W1 in the range of 100° to 120°, more preferably about 108°, such that the first and second intermediate sidewall portions 240, 245 diverge towards the capsule chamber 30.

The first supporting wall portion 50 forms a horizontal wall of a first capsule support having a triangular shape. The first capsule support 250 comprises two sidewalls 255 converging at a lower tip 260.

A vertical distance E between the bottom wall 230 and the lower tip 260 of the first capsule support 250 is preferably in the range of 5 mm to 10 mm, more preferably about 8.5 mm. A vertical height F of the first capsule support 250 between the lower tip 260 and the first supporting wall portion is preferably in the range of 2 mm to 7 mm, more preferably about 5 mm. Both sidewalls 255 preferably enclose an angle W2 at the lower tip 260 in the range of 70° to 90°, more preferably about 78°.

A vertical height G of the capsule chamber 30 between the first supporting wall portion 50 and the second supporting wall portion 55 is preferably in the range of 3 mm to 9 mm, more preferably about 6.4 mm. The horizontal width H of the capsule chamber 30 between the first and second sidewall portions 60, 65 is preferably in the range of 15 mm to 20 mm, more preferably 18.8 mm. The first and second outlet ducts 120, 125 preferably have a width I in the range of 1 mm to 6 mm, preferably about 3.7 mm.

It has to be understood that the inhaler device according to the present embodiment may comprise any of the first and second outlet ducts 120, 125 as described with reference to FIGS. 1 to 14 no matter which shape and run they have. It has to be further understood that the second supporting side wall 55 may be part of a second capsule support having a triangular or semicircular form or curved shape or rectangular shape as shown in the FIGS. 1 to 14.

The invention claimed is:

1. An inhaler device comprising
an inhaler housing comprising one air inlet duct;
an elongated capsule chamber adapted for receiving a capsule which contains a dose of medicament in dry powder form, and wherein the capsule chamber has a longitudinal axis and is defined by a wall arrangement including a first and a second supporting wall portion opposing each other in a direction perpendicular to the longitudinal axis and first and second sidewall portions opposing each other in the direction of the longitudinal axis;
a mouthpiece portion through which the medicament in dry powder form is dispensable; and
at least first and second airflow paths which extend between the air inlet duct, the capsule chamber and the mouthpiece portion to enable an inhalation airflow formed upon inhalation to flow through the air inlet duct via the capsule chamber and the mouthpiece portion such that the dose of medicament is entrained in air and dispensed through the mouthpiece portion;
wherein the first and second airflow paths are arranged such that during inhalation, the capsule having a longitudinal axis and first and second end sections delimiting the capsule on opposing ends located in the capsule chamber performs an oscillating movement in the capsule chamber parallel to the longitudinal axis of the capsule chamber between the first and the second sidewall portions when the inhalation airflow is initiated through the at least first and the second airflow paths in a direction from the air inlet duct towards the mouthpiece portion,
wherein the first airflow path comprises at least a first intermediate duct extending from the air inlet duct to a first capsule chamber inlet adjacent to the first sidewall portion, and at least a first outlet duct extending from a first capsule chamber outlet adjacent to the first sidewall portion to the mouthpiece portion; and the second airflow path comprises at least a second intermediate duct extending from the air inlet duct to a second capsule chamber inlet adjacent to the second sidewall portion, and at least a second outlet duct extending from a second capsule chamber outlet adjacent to the second sidewall portion to the mouthpiece portion; and wherein the air inlet duct discontinuously expands prior to its connection with the at least first and second airflow paths to cause the inhalation airflow formed upon inhalation to form an air jet which is attracted to flow either along a first intermediate sidewall portion of the first intermediate duct or alternatively to flow along a second intermediate sidewall portion of the second intermediate duct such that the air jet either streams into the first or second airflow path, respectively.

2. The inhaler device of claim 1, further comprising a moveable piercing means located in the first and second sidewall portions of the capsule chamber for piercing the capsule located in the capsule chamber at its first and second end sections.

3. The inhaler device of claim 2, wherein the first and second intermediate ducts taper in direction from the air inlet duct to the first and second capsule chamber inlets.

4. The inhaler device of claim 2, wherein the first and second outlet ducts expand in direction from the first and second capsule chamber outlets to the mouthpiece portion.

5. The inhaler device of claim 4, wherein the first and second outlet ducts continuously expand in direction from the first and second capsule chamber outlets to the mouthpiece portion.

6. The inhaler device of claim 2, wherein the first and second outlet ducts are curved.

7. The inhaler device of claim 6, wherein the first and second outlet ducts are connected to form one continuous curve having an apex, wherein the mouthpiece portion is connected to the apex of the curve formed by the first and second outlet ducts.

8. The inhaler device of claim 6, wherein the first and second outlet ducts are connected to form a wavy form comprising two crests and one trough, wherein the mouthpiece portion is connected to the trough.

9. The inhaler device of claim 1, wherein the inlet duct comprises a first inlet sidewall portion and a second inlet sidewall portion which taper towards an inlet opening such that a flow cross-section formed by the first and second inlet sidewall portions decreases towards the inlet opening and discontinuously expands herein after.

10. The inhaler device of claim 9, wherein the first inlet sidewall portion and the second inlet sidewall portion tapering towards the inlet opening cease to converge towards each other to converge with a bottom wall.

11. The inhaler device of claim 9, wherein the first inlet sidewall portion and the second inlet sidewall portion tapering towards the inlet opening converge with first and second parallel walls then extend to and converge with a bottom wall.

12. The inhaler device of claim 1, further comprising a first inlet loop duct extending from a region within the first intermediate duct to the air inlet duct, and a second inlet loop duct extending from a region within the second intermediate duct to the air inlet duct.

13. The inhaler device of claim 12, wherein the first and second inlet loop ducts narrow prior to their connection with the air inlet duct.

14. The inhaler device of claim 2 further comprising an outlet loop duct extending from the first capsule chamber outlet adjacent to the first sidewall portion and the first outlet duct to the second capsule chamber outlet at the proximity of the second sidewall portion and the second outlet duct.

15. Method of delivering a dose of medicament in dry powder form from a capsule to a patient in need thereof comprising:

a) providing the capsule having a longitudinal axis and first and second end sections which contains the dose of medicament in dry powder form;
b) providing an inhaler device according to claim 1;
c) inserting the capsule into the capsule chamber of the inhaler device;
d) piercing openings at the first and second end sections of the capsule using a movable piercing means;
e) inhaling through the mouthpiece portion such that an inhalation airflow is formed flowing through the air inlet duct via the capsule chamber and the mouthpiece portion into the patient's lungs, wherein the capsule located in the capsule chamber performs an oscillating movement in the capsule chamber parallel to its longitudinal axis between the first and the second sidewall portions when the inhalation airflow is initiated through the first and the second airflow paths in a direction from the air inlet duct towards the mouthpiece portion.

16. The inhaler device of claim 3, wherein the first and second outlet ducts expand in direction from the first and second capsule chamber outlets to the mouthpiece portion.

17. The inhaler device of claim 16, wherein the first and second outlet ducts continuously expand in direction from the first and second capsule chamber outlets to the mouthpiece portion.

* * * * *